US00PP28063P3

(12) United States Plant Patent
Eveleens

(10) Patent No.: US PP28,063 P3
(45) Date of Patent: May 30, 2017

(54) ***HYDRANGEA* PLANT NAMED 'HORTMAGRECLO'**

(50) Latin Name: *Hydrangea macrophylla*
Varietal Denomination: HORTMAGRECLO

(71) Applicants: Horteve Breeding BV, De Kwakel (NL); Kolster Holding BV, Boskoop (NL)

(72) Inventor: Cornelis Pieter Eveleens, Aalsmeer (NL)

(73) Assignees: HORTEVE BREEDING BV, Aalsmeer (NL), part interest; KOLSTER HOLDING BV, Boskoor (NL), part interest ( * ) Notice: Subject to any disclaimer, the term of this patent is extended or adjusted under 35 U.S.C. 154(b) by 167 days.

(21) Appl. No.: 14/756,021

(22) Filed: Jul. 22, 2015

(65) Prior Publication Data

US 2016/0183430 P1 Jun. 23, 2016

(30) Foreign Application Priority Data

Dec. 23, 2014 (EM) ..... 2014/3568

(51) Int. Cl.
*A01H 5/00* (2006.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Hydrangea macrophylla* plant named, 'HORTMAGRECLO', that is characterized by its inflorescences with a flattened globular shape, its floriferous bloom habit, its sterile flowers with sepals are green in color when mature and become darker green as they age, and its strong stems.

2 Drawing Sheets

Botanical classification: *Hydrangea macrophylla.*
Varietal denomination: 'HORTMAGRECLO'.

BACKGROUND OF THE INVENTION

The present invention relates to a new and distinct cultivar of *Hydrangea macrophylla* and will be referred to hereafter by its cultivar name, 'HORTMAGRECLO'. 'HORTMAGRECLO' represents a new mophead type *Hydrangea*, a deciduous shrub grown for use as a landscape plant and as a cut flower.

The new cultivar was derived from an ongoing controlled breeding program conducted by the Inventor in Boskoop, The Netherlands. The goal of the breeding program is to develop new cultivars of *Hydrangea* with good cut flower qualities that include strong stems, long lasting flowers, and attractive foliage. 'HORTMAGRECLO' was derived from a cross made in May of 2010 between proprietary plants from the Inventor's breeding program reference no. 08-038-06 (not patented) as the female parent and reference no. 08-031-03 (not patented) as the male parent. 'HORTMAGRECLO' was selected in 2013 as a single unique plant from amongst the resulting seedlings.

Asexual propagation of the new cultivar was first accomplished by stem cuttings in Boskoop, The Netherlands by the Inventor in July 2012. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'HORTMAGRECLO' as a unique cultivar of *Hydrangea.*

1. 'HORTMAGRECLO' exhibits inflorescences with a flattened globular shape.
2. 'HORTMAGRECLO' exhibits a floriferous bloom habit.
3. 'HORTMAGRECLO' exhibits sterile flowers with sepals that are serrated are green in color when mature and become darker green as they age.
4. 'HORTMAGRECLO' exhibits strong stems.

The female parent of 'HORTMAGRECLO', differs from 'HORTMAGRECLO' in having sterile flowers with sepals that are soft pink suffused with green in color and in having sepals with entire margins. The male parent of 'HORTMAGRECLO', differs from 'HORTMAGRECLO' in having sterile flowers with sepals that are dark pink with very little green suffusion in color and in having inflorescences that are more globular in shape. 'HORTMAGRECLO' can be most closely compared to the *Hydrangea* cultivars 'Green Shadow (not patented) and 'Hokomac' (U.S. Plant Pat. No. 22,259). 'Green Shadow' is similar to 'HORTMAGRECLO' in having inflorescences with a flattened globular shape. 'Green Shadow' differs from 'HORTMAGRECLO' in having sterile flower sepals that are dark pink suffused with green in color and in having sepals with entire margins. 'Hokomac' is similar to 'HORTMAGRECLO' in having inflorescences with a flattened globular shape. 'Hokomac' differs from 'HORTMAGRECLO' in having sterile stems with sepals that are a blend of pink and green in color.

BRIEF DESCRIPTION OF THE DRAWINGS

The accompanying colored photographs illustrate the overall appearance and distinct characteristics of the new

*Hydrangea*. The photographs were taken of a three year-old plant of 'HORTMAGRECLO' as grown in a 23-cm container in a greenhouse in Boskoop, The Netherlands.

Figure 1:
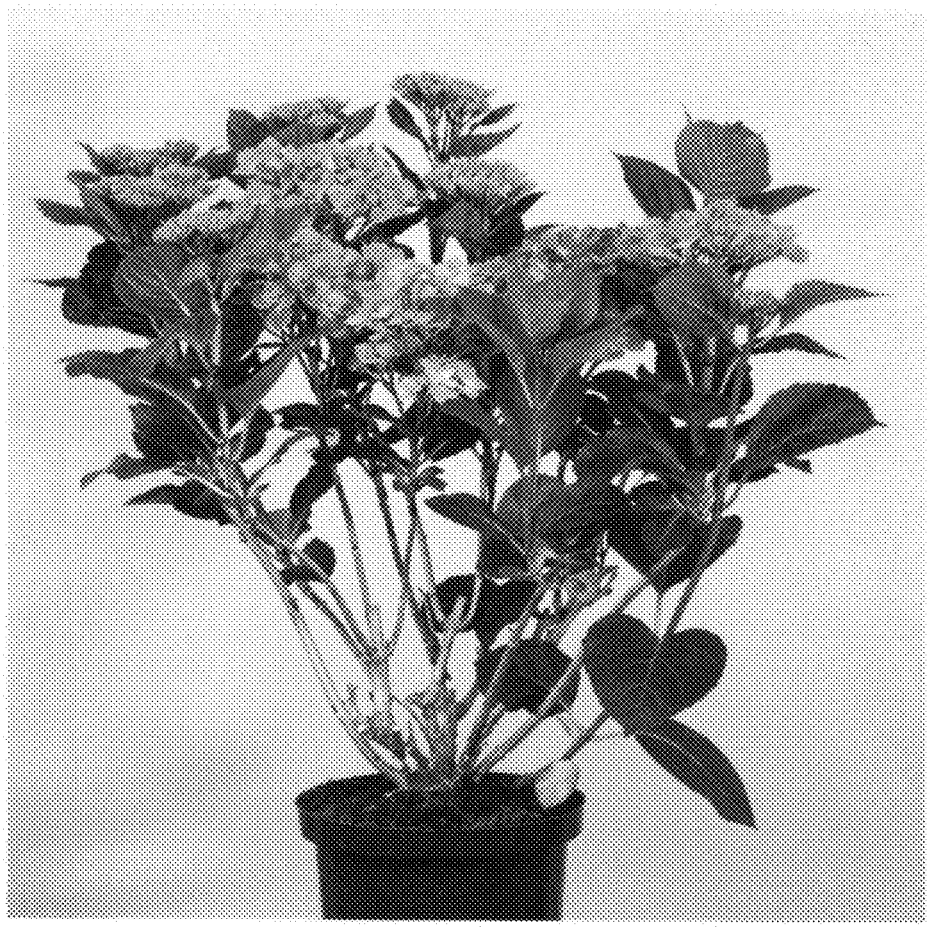

The photograph in FIG. 1 provides a side view of the plant habit of 'HORTMAGRECLO' in bloom.

Figure 2:
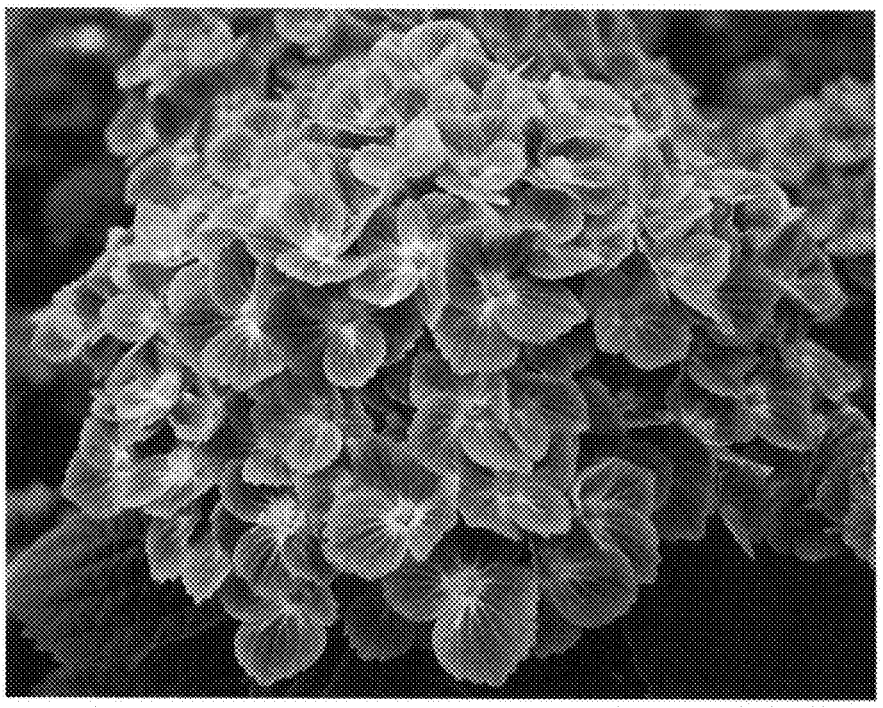

The photograph in FIG. 2 provides a close-up view of an inflorescence of 'HORTMAGRECLO'.

Figure 3:
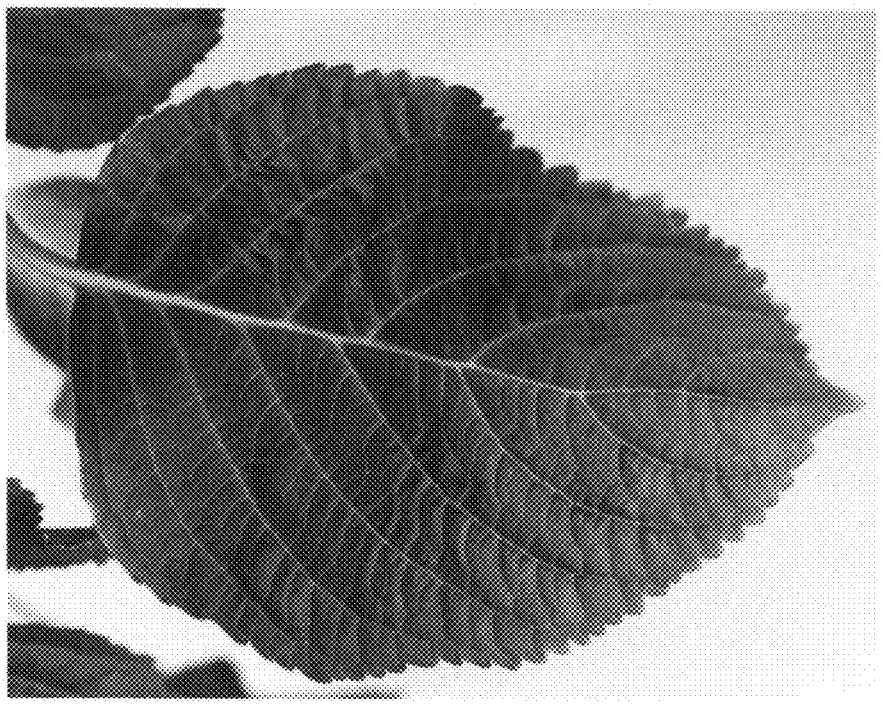

The photograph in FIG. 3 provides a close-up view of a leaf of 'HORTMAGRECLO'.

The colors in the photographs are as close as possible with the photographic and printing technology utilized and the color values cited in the Detailed Botanical Description accurately describe the colors of the new *Hydrangea*.

DETAILED BOTANICAL DESCRIPTION

The following is a detailed description of three year-old plants of 'HORTMAGRECLO' as grown in a greenhouse in 23-cm containers in Boskoop, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period*.—From May to November in a greenhouse in Boskoop, the Netherlands.

*Plant type*.—Deciduous shrub, mophead type *Hydrangea*.

*Plant habit*.—Broad upright.

*Height and spread*.—An average of 100 cm in height and 60 cm in spread.

*Hardiness*.—At least U.S.D.A. Zones 5 to 9.

*Diseases resistance*.—No susceptibility and resistance has been observed.

*Root description*.—Fine and fibrous.

*Propagation*.—Stem cuttings.

*Root development*.—An average of 6 months at average air temperatures of 15 to 25° C. to finish a young plant.

*Growth rate and vigor*.—Moderate.

Stem description:

*Stem shape*.—Rounded.

*Stem strength*.—Strong.

*Stem color*.—New growth; 144A to 144B suffused with N187C at the nodes, mature growth; a blend of 165B to 165C and N199D.

*Stem size*.—An average of 24.2 cm in length and 8 mm in diameter.

*Stem surface*.—Glabrous, moderately lenticellate, lenticels; 6 per $cm^2$, an average of 2.5 mm in length and 1 mm in width, N186C in color.

*Stem aspect*.—Held at an average angle of 55° to horizontal.

*Internode length*.—An average of 6.6 cm.

*Branching*.—Moderately freely branching with an average of 14 lateral branches.

Foliage description:

*Leaf shape*.—Ovate to broadly ovate.

*Leaf arrangement*.—Opposite.

*Leaf division*.—Simple.

*Leaf base*.—Obtuse to short attenuate.

*Leaf apex*.—Broad apiculate.

*Leaf margins*.—Serrate.

*Leaf venation*.—Pinnate, color; upper surface 144B and lower surface a blend of 144B and 145A.

*Leaf size*.—An average of 11.6 cm in length and 9.4 cm in width.

*Leaf attachment*.—Petiolate.

*Leaf surface*.—Both surfaces; glabrous and slightly rugose.

*Leaf color*.—Young foliage upper surface; 137A and lower surface; 147B, mature foliage upper surface; a color between N137A and 147A and lower surface; 147B.

*Petioles*.—An average of 3.6 cm in length and 3.5 mm in diameter, color; upper surface 145A and lower surface 144B, both surfaces glabrous and glossy to moderately glossy.

Inflorescence description:

*Inflorescence type*.—Terminal panicle, flattened mophead in form comprised of a center region of fertile flowers surrounded by numerous single sterile flowers.

*Lastingness of inflorescence*.—Sterile flowers; persistent for an average of 6 weeks, fertile flowers; an average of 5 days, self-cleaning.

*Inflorescence number*.—One per lateral stem.

*Inflorescence size*.—An average of 14.8 cm in height and 17.9 cm in diameter.

*Flower number*.—An average of 180 sterile flowers and 60 fertile flowers per panicle.

*Flower fragrance*.—None.

*Flower aspect*.—Upright to slightly outward.

*Flower size*.—Sterile flowers; an average of 4.2 cm in diameter and 2 cm in depth, fertile flowers; an average of 4 mm in diameter and 5 mm in depth.

*Flower type*.—Rotate.

*Flower buds*.—Sterile flowers; an average of 6 mm in length and 4 mm in diameter, ovate in shape, color; 143A with base 144B, fertile flowers; an average of 4 mm in length and 3 mm in diameter, broad obovate in shape, color; 143B with base 144B.

*Peduncles*.—Strong, an average of 5 cm in length and 4 mm in width, 144A to 144B in color, dull surface is sparsely covered with short soft hairs an average of 0.5 mm in length and 157D in color.

*Pedicels*.—Sterile flowers; held at an average angle of 25° from peduncle, an average of 3.3 cm in length and 1.75 mm in diameter, strong strength, color; a blend of 65D and N155C, lenticellate, lenticels; an average of 1 mm in length and 0.5 mm in width, a blend between 53A and 184B in color, dull surface sparsely covered with short soft hairs an average of 0.5 mm in length and N155B in color, fertile flowers; held at an average angle of 25° from vertical, an average of 4 mm in length and 1 mm in diameter, moderate strength, color; 145B to 145C, dull surface is sparsely covered with short soft hairs an average of 0.5 mm in length and 157D in color.

*Petals*.—Sterile flowers; an average of 4, rotate arrangement, acute apex, cuneate base, entire margins, ovate and concave in shape, an average of 4 mm in length and 2 mm in width, both surfaces; glabrous and dull, color; upper and lower surfaces when opening NN155D with apex 157C to 157D, upper and lower surfaces when fully opened NN155D with apex 155B, color not fading, fertile flowers; an average of 4, rotate in arrangement, ovate and slightly concave in shape, entire margin, acute apex, cuneate base, an average of 4 mm in length and 3 mm in width, upper and lower surface glabrous and dull, color; upper and lower surface when opening 143B and when fully 143B to 143C, color not fading.

*Sepals*.—Sterile flowers; an average of 6, rotate arrangement, broad rhomboidal to ovate in shape, an average of 2.4 cm in length and 2.1 cm in width, broadly acute apex, serrated margin (average of three teeth per side), obtuse to short cordate base, upper surface moderately rugose, glabrous, and dull, lower surface glabrous and dull, color; when opening upper surface 145A and lower surface 145B, when fully opened upper surface 144A to 144B with veins 157D and lower surface; a blend between 145B and 147D, color fades to 137A on upper surface and 147D on lower surface, fertile flowers; an average of 5, rotate in arrangement, ovate in shape, entire margin, acute apex, broadly cuneate base, an average of 2 mm in length and 0.1 mm in width, both surfaces are glabrous and dull, color; upper and lower surface when opening 144B and when fully opened 143C, color not fading.

Reproductive organs: (Present on fertile flowers and occasionally on sterile flowers).

*Stamens*.—Sterile flowers; an average of 6, anther; broad kidney-shaped, an average of 1 mm in length, and 155D in color, filament; an average of 4 mm in length and NN155D in color, pollen is moderate in quantity and 155A in color, fertile flowers; an average of 8, anther; broad kidney-shaped, an average of 0.75 mm in length and 145B in color, filament; an average of 2 mm 145A in color, pollen is not present (anthers do not mature).

*Pistils*.—Sterile flowers; an average of 2, an average of 2 mm in length, stigma; club-shaped and NN155C in color, style is an average of 1 mm in length and 155A in color, ovary is 155A in color, fertile flowers; an average of 3, an average of 1.5 mm in length, stigma; club-shaped and 145C to 145D in color, style; an average of 1 mm in length and 145B to 145C in color, ovary is 145B in color.

*Fruit and seed*.—None observed.

It is claimed:

1. A new and distinct cultivar of *Hydrangea* plant named 'HORTMAGRECLO' as herein illustrated and described.

* * * * *